United States Patent
Liu et al.

(10) Patent No.: US 10,231,812 B2
(45) Date of Patent: Mar. 19, 2019

(54) ADJUSTMENT ASSEMBLY OF RESPIRATORY MASK

(71) Applicant: BMC Medical Co., Ltd., Shingshan, Beijing (CN)

(72) Inventors: Yi Liu, Beijing (CN); Xingwen Chen, Beijing (CN)

(73) Assignee: BMC Medical Co., Ltd. (CN)

( * ) Notice: Subject to any disclaimer, the term of this patent is extended or adjusted under 35 U.S.C. 154(b) by 648 days.

(21) Appl. No.: 14/143,942

(22) Filed: Dec. 30, 2013

(65) Prior Publication Data

US 2014/0109913 A1    Apr. 24, 2014

Related U.S. Application Data

(63) Continuation of application No. PCT/CN2012/075248, filed on May 9, 2012.

(30) Foreign Application Priority Data

Jun. 30, 2011 (CN) .......................... 2011 1 0181592

(51) Int. Cl.
*A61M 16/06* (2006.01)
*A61D 7/00* (2006.01)
*A61M 16/08* (2006.01)

(52) U.S. Cl.
CPC ............... *A61D 7/00* (2013.01); *A61M 16/06* (2013.01); *A61M 16/0644* (2014.02); *A61M 16/0683* (2013.01); *A61M 16/0816* (2013.01)

(58) Field of Classification Search
CPC ..... A61D 7/00; A61M 16/0644; A61M 16/06; A61M 16/0683; A61M 16/0816; A61M 16/0605; A62B 18/02; A62B 18/084

USPC ............ 128/207.18, 206.27, 201.22, 201.23, 128/201.24, 201.29, 203.29, 205.25, 128/206.12, 206.24, 206.28, 207.11, 128/207.17, 204.18

See application file for complete search history.

(56) References Cited

U.S. PATENT DOCUMENTS

| | | | |
|---|---|---|---|
| 6,926,004 B2 * | 8/2005 | Schumacher ..... | A61M 16/0633 128/201.22 |
| 8,505,535 B2 * | 8/2013 | Jones ................... | A61M 16/06 128/204.21 |
| 2004/0045551 A1 | 3/2004 | Eaton et al. | |
| 2005/0072428 A1 * | 4/2005 | Ho ....................... | A61M 16/06 128/205.25 |
| 2006/0272646 A1 * | 12/2006 | Ho ..................... | A61M 16/0683 128/207.11 |

(Continued)

FOREIGN PATENT DOCUMENTS

| | | |
|---|---|---|
| CN | 201120227654.X | 2/2012 |
| CN | 201110181592.8 | 1/2013 |

(Continued)

*Primary Examiner* — Gregory Anderson
*Assistant Examiner* — Margaret Luarca
(74) *Attorney, Agent, or Firm* — Omair M. Farooqui; Aziz M. Ahsan; Palo Alto Legal Group, P.C.

(57) ABSTRACT

An adjustment assembly of a respiratory mask is provided and includes: a forehead fixing device, adapted to fix the respiratory mask on a user's forehead; an adjustment device, comprising a base body and connectors set on the base body, wherein, at least one connector is chosen by a user to be connected with the forehead fixing device according to the user's forehead.

17 Claims, 8 Drawing Sheets

(56) References Cited

U.S. PATENT DOCUMENTS

2009/0223521 A1* 9/2009 Howard ............... A61M 16/06
                                                    128/206.23

FOREIGN PATENT DOCUMENTS

EP    12804515.0         5/2014
WO  PCT/CN2012/075248    1/2013

* cited by examiner

ADJUSTMENT ASSEMBLY OF RESPIRATORY MASK

CROSS-REFERENCE TO RELATED APPLICATION

The application is a continuation of PCT/CN2012/075248 (filed on Sep. 5, 2012), which claims priority of Chinese patent application 201110181592.8 (filed on Jun. 30, 2011), the contents of which are incorporated herein by reference.

FIELD OF THE INVENTION

The present invention is related to medical mask technology for the sleep-disordered breathing (SDB) treatment, especially related to an adjustment assembly of a respiratory mask.

BACKGROUND OF THE INVENTION

Respiratory mask has been widely used to provide continuous positive airway pressure (CPAP) to cure various respiratory diseases and SDB, such as obstructive sleep apnea (OSA), and/or provide other ventilation treatments such as non-invasive positive pressure ventilation (NIPPV). The SDB treatment device normally includes a ventilator which transmits the positive pressure air to the user interface via an airway tube. The user interface may be a respiratory mask used on the nose or snout. Generally speaking, the respiratory mask includes a soft mask assembly in touch with the user's face and a rigid main frame. A chamber accommodating the nose or snout is formed by the main frame and the mask assembly consequently. The respiratory mask is fixed properly on the user's face by using a bandage device, which for instance binding across from the two sides of the user's face to the back or top of the user's head.

Since wearing the respiratory mask during sleep may cause asymmetric pressure on the user's face and may cause air leakage consequently, and to provide comfortable wearing experience, a forehead fixing device may also be set on the main frame. The forehead fixing device can provide a stable support via a support point between the respiratory mask and the user's forehead. As a result, the moving range of the mask is minimized and the wearing experience is improved.

However, different users have different facial features. In order to fit the heights of different users' foreheads, the forehead fixing device has to be adjustable. Though in the prior art, there already have some kinds of respiratory masks with adjustable forehead fixing devices, the structures are too complex and the manufacture processes are difficult and costly due to mass of parts. Therefore, an improvement of the respiratory mask is required.

Consequently, a new kind of respiratory mask and an adjustment assembly thereof are required to solve the problems mentioned above.

SUMMARY OF THE INVENTION

One objective of the present invention provides an adjustment assembly of a respiratory mask The adjustment assembly of a respiratory mask provided includes:

a forehead fixing device, adapted to fix the respiratory mask on a user's forehead;

an adjustment device, comprising a base body and connectors set on the base body, wherein, at least one connector is chosen by a user to be connected with the forehead fixing device according to the user's forehead.

according to the technical scheme of the present invention, by setting multiple connectors which can be connected to the forehead fixing device and allow a connector to be chosen from the multiple connectors and be connected with the forehead fixing device according to a user's forehead, the respiratory mask can fit different users' foreheads to avoid the air leakage caused by the mask motion during user's sleeping. Furthermore, the structure and manufacture process of the adjustment assembly in the present invention are simplified, less parts or pieces are included, and the costs greatly reduce.

BRIEF DESCRIPTION OF THE DRAWINGS

The following figures, as a part of the present invention, are provided to facilitate the understanding of the present invention. The embodiments and the descriptions in the following figures are provided to illustrate the principle of the present invention.

DETAILED DESCRIPTION OF THE INVENTION

Specific details are provided to facilitate the understanding of the present invention. Those skilled in the art can understand that the invention may be implemented without one or multiple features. In some embodiment, in order to avoid confusion, some features well known in the art will not be described.

This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as systems, methods or devices. The following detailed description should not to be taken in a limiting sense.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on". The term "coupled" implies that the elements may be directly connected together or may be coupled through one or more intervening elements. Further reference may be made to an embodiment where a component is implemented and multiple like or identical components are implemented.

While the embodiments make reference to certain events this is not intended to be a limitation of the embodiments of the present invention and such is equally applicable to any event where goods or services are offered to a consumer. The detail structures will be described to provide a thorough understanding of the present invention. Apparently, the implementation of the present invention is not limited by the specific details well known by those skilled in the art. A preferred embodiment will be described as follows; however, there are many other embodiments.

A further description of the technical scheme proposed in the present invention will be given hereinafter with reference to the accompanying drawings.

Figure 1A:
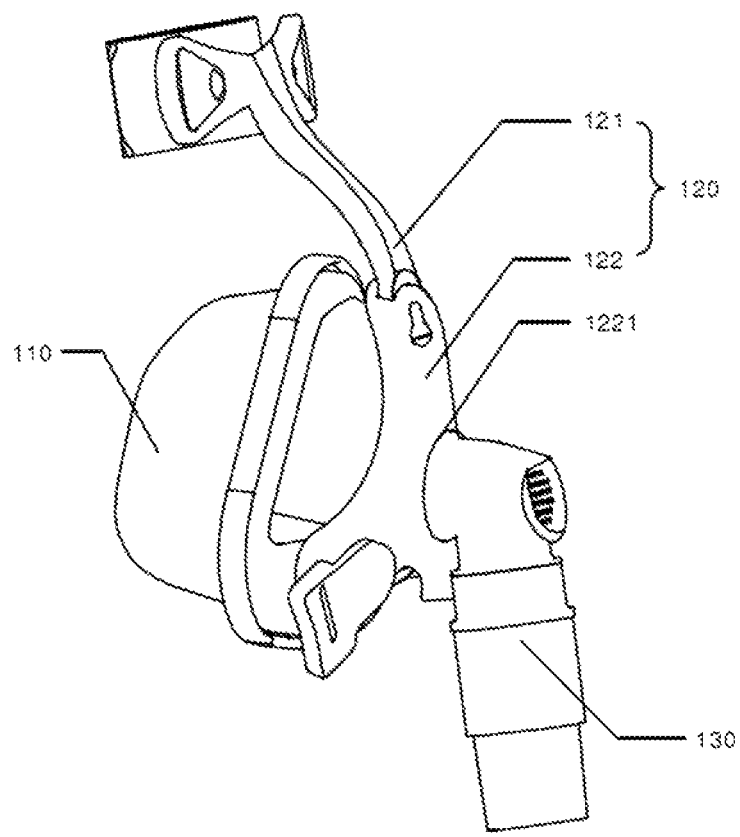
FIG. 1A illustrates the solid view of a respiratory mask in an embodiment of the present invention.
Figure 1B:
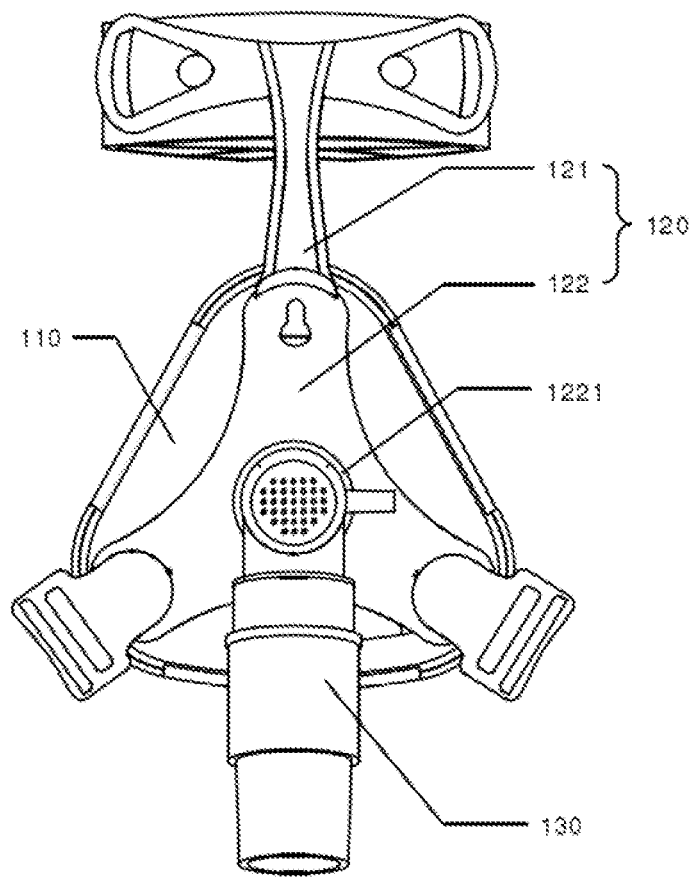
FIG. 1B illustrates the main view of a respiratory mask in an embodiment of the present invention.
Figure 1C:
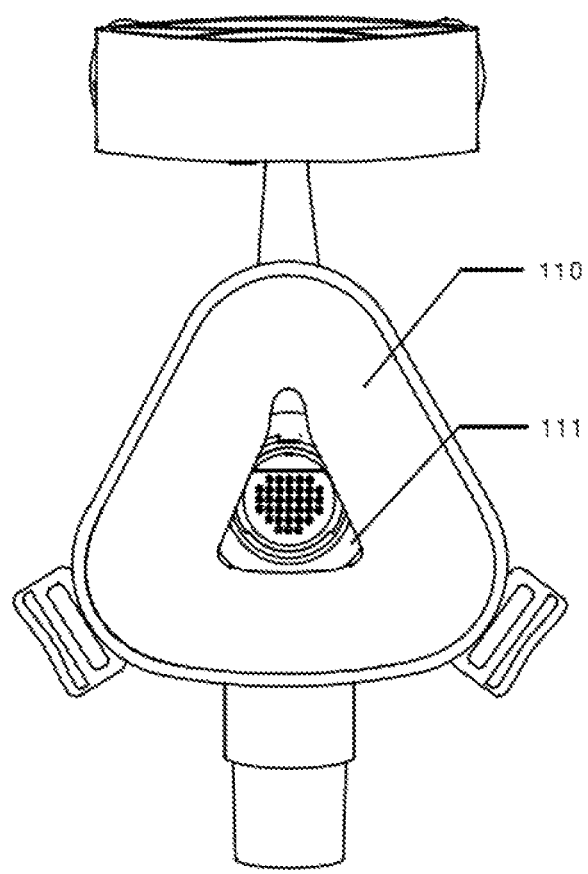
FIG. 1C illustrates the rear view of a respiratory mask in an embodiment of the present invention.

FIG. 1A illustrates the solid view of a respiratory mask 100 in an embodiment of the present invention. FIG. 1B illustrates the 100 in an embodiment of the present invention. FIG. 1C illustrates the rear view of the respiratory mask 100 in an embodiment of the present invention. As shown in FIG. 1A~FIG. 1C, the respiration mask 100 includes a mask assembly 110 and an adjustment assembly 120 provided to adjust the respiratory mask 100. The mask assembly 110 includes a chamber 111 for accommodating the nose or snout. To make the mask be worn comfortably, the mask assembly 110 may be made of soft materials. Furthermore, the adjustment assembly 120 includes a forehead fixing device 121 and an adjustment device 122 connected with the forehead fixing device 121. The forehead fixing device 121 is used to fix the respiratory mask 100 on the user's forehead. The adjustment device 122 is used to adjust the position of the forehead fixing device 121 relative to the user's forehead to make the mask fit the foreheads of different users and avoid the air leakage caused by the mask motion during users' sleeping. To facilitate the understanding and description of the present invention, firstly the assemblies included in the adjustment assembly 120 will be described, and then a detailed description will be illustrated with reference to the connection between the adjustment assembly 120 and the mask assembly 110.

Figure 2:
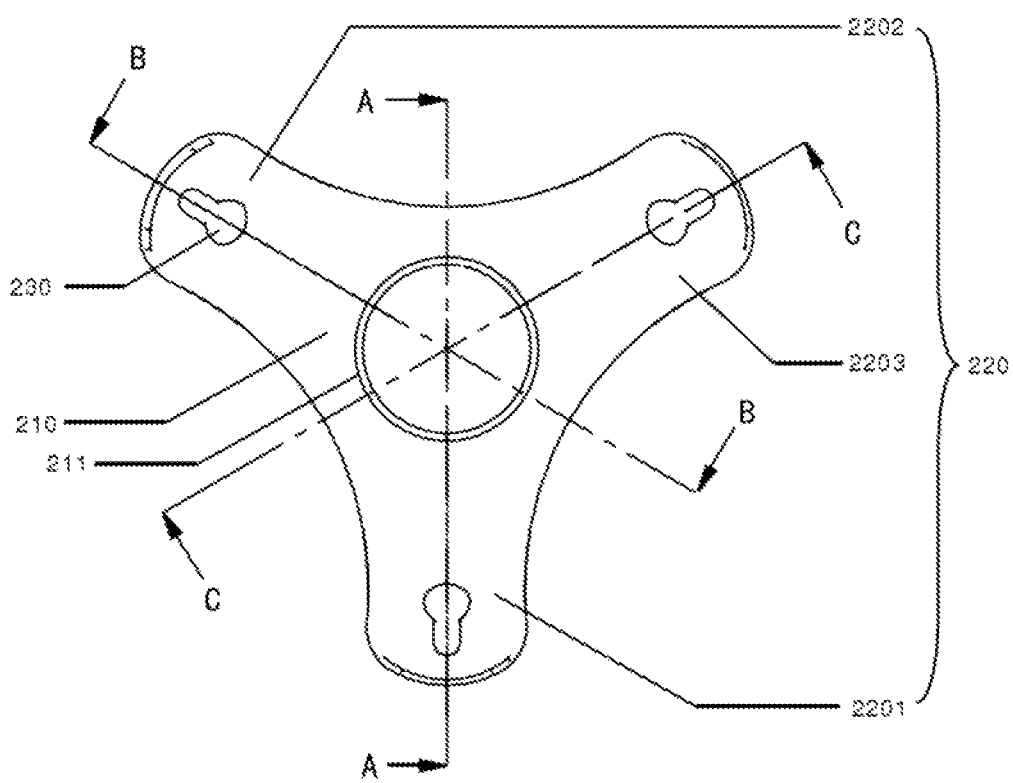
FIG. 2 illustrates the main view of an adjustment assembly in an embodiment of the present invention.

FIG. 2 illustrates the main view of an adjustment assembly in an embodiment of the present invention. As shown in FIG. 2, the adjustment device 200 includes a base body 210 and several connectors 220 set on the base body 210. The base body 210 and connectors 220 may be integrated or separated. It is preferable that the base body 210 and connectors 220 are integrated, which will reduce the parts number, simplify the manufacture process and improve the connection strength between the base body 210 and connectors 220 to extend the service life of the adjustment device 200. Three connectors (2201, 2202 and 2203) on the adjustment device 200 are illustrated in FIG. 2, however, the number of the connectors shown in FIG. 2 is not used to limit the scope of the present invention. The number of connectors 220 may be 2, 4 or even more. Since each connector 220 is used to connect the adjustment device 200 with the forehead fixing device (shown as 121 in FIG. 1A~1B), each connector can be connected with the forehead fixing device, so that the user may choose one or more proper connectors being connected with the forehead fixing device according to his/her forehead while wearing the respiratory mask.

As an example, the connection between each connector 220 and the forehead fixing device may be detachable. In this case, to make the connection detachable, a connector matching piece (e.g. 240 shown in FIG. 3A~3C and FIG. 4A~4C) and a forehead fixing matching piece (e.g. 540 shown in FIG. 5A~5B) are set on each connector 220 and the forehead fixing device respectively. The connector matching piece and the forehead fixing matching piece may be any match pieces in any assemble form, such as a plug and groove used for plugging, a nut and bolt used for screwing, or a hole and protruding piece used for snapping, which can be used for detachable connection. Furthermore, the matching pieces set on each connector 220 and the forehead fixing device may exchange with each other. For example, when the connector matching piece is a plug, the forehead fixing matching piece is a groove; while when the connector matching piece is a groove, the forehead fixing matching piece is a plug. In order to facilitate the manufacture and usage, the connector matching piece and the forehead fixing matching piece are preferably be the plug and groove. The description in FIG. 3A-3C, FIG. 4A-4C, FIG. 5A-5B and following contents will take the plug and groove as an example to illustrate the principle of the present invention.

In addition, a bandage connector 230 may be provided on the connector 220 to connect with a bandage device. The bandage device may be a prior device which fixes the respiratory mask on the user's face by binding across from the two sides of the user's face to the back of the user's head. Moreover, the bandage device may be of any other structures with the fixing function. To further improve the stability of the mask while being worn, a bandage connector may also be set on the forehead fixing device. It should be noticed that, the bandage connectors set on the connector 220 and the forehead fixing device may have the same or different structures. Those skilled in the art can understand that the bandage connectors may adapt a variety of structures to be connected with the connector 220 and the forehead fixing device.

In a preferable embodiment of the present invention, the adjustment device 200 includes three connectors 220, i.e., the first connector 2201, the second connector 2202 and the third connector 2203. When the three connectors are set on the base body 210, one is used as an adaptation connector to be connected with the forehead fixing device, and the other two are used to be connected with the bandage device. Preferably, the shape of the base body 210 is circular, the first connector 2201, the second connector 2202 and the third connector 2203 are located on the outer circle of the base body 210 with the same interval, to fit the shape of the human head, and make the bandage device extend back from a side of the head to the underside of the rear which greatly improve the wearing experiences. In addition, since different users may choose different connectors as the adaption connector, it is preferable that a bandage connector 230 is provided for each connector. When the mask is worn, one of the connectors is connected with the forehead fixing device while the other two are connected with the bandage device via the bandage connectors 230.

Preferably, a through hole 211 is set on the center of the base body 210 to connect with one end of an airway tube (shown as 130 in FIG. 1A~1B). Setting the through hole 211 on the center of the base body 210 greatly simplifies the structure of the respiratory mask and it is more convenient for a user to put (e.g. by rotating) the adaption connector chosen from multiple connectors on a proper position, to make the forehead fixing device fit the user's head well.

The structure of the connectors used for adjusting will be described in detail hereinafter.

Angles between the connector matching pieces and the horizontal ray O-M respectively are adjustable; herein, the horizontal ray extends horizontally from the center of the base body to the user. The adjustment device can adjust the position of the forehead fixing device relative to the user's head by adjusting the angles.

Figure 3A:
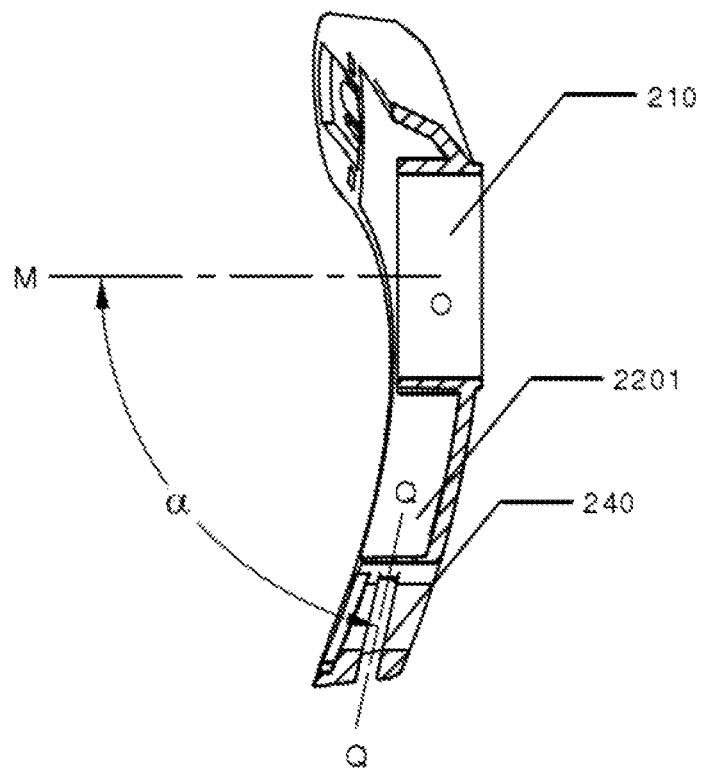
FIG. 3A illustrates the sectional view taken along the A-A line in FIG. 2 in an embodiment of the present invention.
Figure 3B:
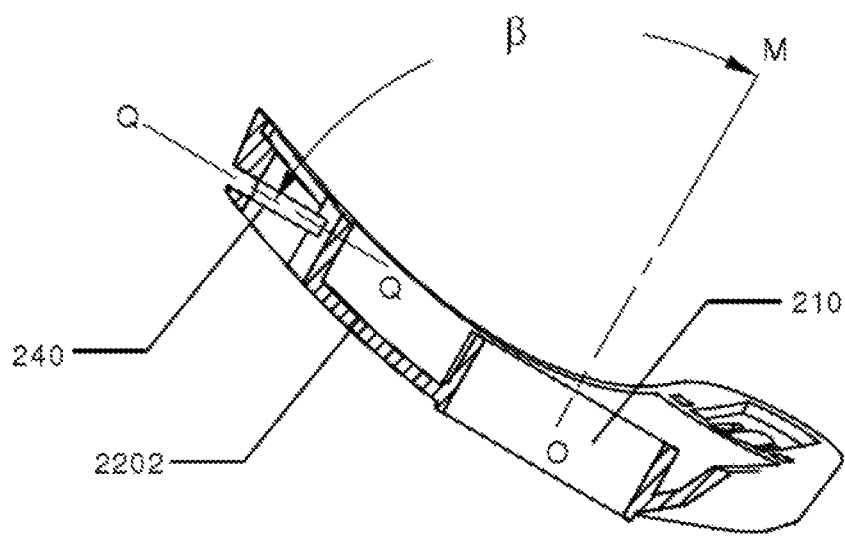
FIG. 3B illustrates the sectional view taken along the B-B line in FIG. 2 in an embodiment of the present invention.
Figure 3C:
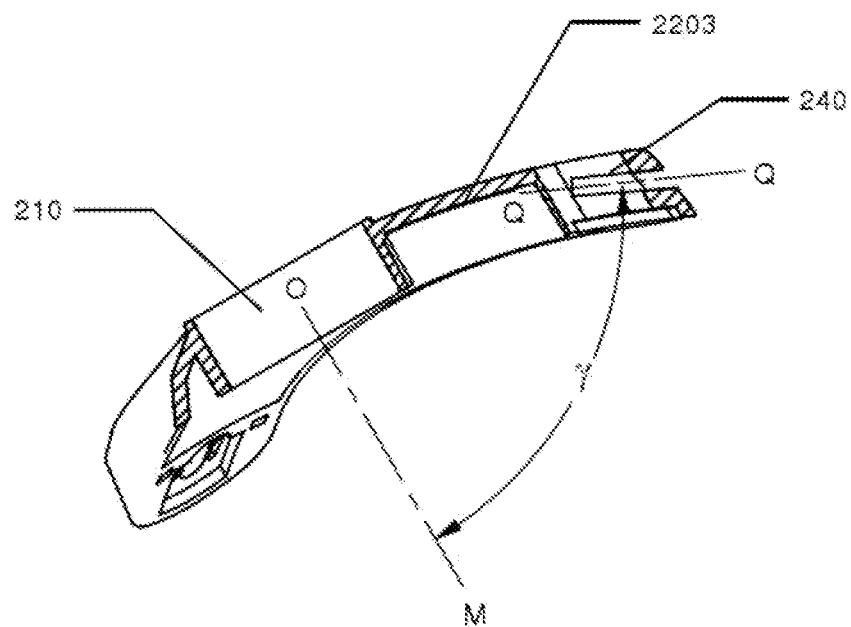
FIG. 3C illustrates the sectional view taken along the C-C line in FIG. 2 in an embodiment of the present invention.

In an embodiment of the present invention, as shown in FIG. 3A~3C, the angles between each connector matching piece 240 that set on each connector (such as 2201,2202 and/or 2203, etc.) and the horizontal ray O-M that through the center O of the base body 210 may be different. Herein, the horizontal ray O-M extends horizontally from the center O to the user, i.e., while the user wearing the respiratory mask at stand pose, the ray O-M extends along the horizontal direction from the center O to the user. The angle between a connector matching piece 240 and the horizontal ray O-M can be understood as the angle between the central line Q-Q of the connector matching pieces 240 and the horizontal ray O-M. For example, when the connector matching piece 240 is a groove, its central line Q-Q means the straight line across the center of the groove and paralleling to the opening direction of the groove.

Setting different angles between each connector matching piece and the horizontal ray O-M makes the corresponding forehead fixing device incline differently relative to the horizontal ray O-M, so that the respiratory mask of the present invention can fit different users' forehead. Those skilled in the art can understand that, the number of the connectors is not limited to 3 as shown in FIG. 3A-3C, it may be 2, 4 and even more.

Taken following preferable embodiment (where there are three connectors set on the base body) as an example, the structure of an adjustment device will be described with reference to FIG. 3A-3C. In this embodiment, the adjustment device adjusts the position of the forehead fixing device relative to the user's head by setting angles between the connector matching pieces and the horizontal ray O-M respectively. As shown in FIG. 3A, the angle between the connector matching piece 240 of the first connector 2201 and the horizontal ray O-M is represented as the first angle $\alpha$. Accordingly, as shown in FIG. 3B, the angle between the connector matching piece 240 of the second connector 2202 and the horizontal ray O-M is represented as the second angle $\beta$. As shown in FIG. 3C, the angle between the connector matching piece 240 of the third connector 2203 and the horizontal ray O-M is represented as the third angle $\gamma$. In an embodiment, the values of the angles $\alpha$, $\beta$ and $\gamma$ are different with each other.

In an embodiment, the value of the angles $\alpha$, $\beta$ and $\gamma$ are in a range of 0°~180°. Since the settings of the angles $\alpha$, $\beta$ and $\gamma$ are related to the structure of the forehead fixing device, those skilled in the art can set the angles $\alpha$, $\beta$ and $\gamma$ to proper values according to the structure of the forehead fixing device. The settings of the angles $\alpha$, $\beta$ and $\gamma$ will be illustrated in detail according to the structure of the forehead fixing device hereinafter.

Considering that the height difference of users' foreheads is within a certain range, the difference between the angles $\beta$ and $\alpha$ and the difference between the angles $\alpha$ and $\gamma$ are restricted; so that those skilled in the art can properly set the angles $\alpha$, $\beta$ and $\gamma$ to make the respiratory mask fit most of users according to the angle differences provided by the present invention and the structure of the forehead fixing device. In an embodiment, the difference between the angles $\beta$ and $\alpha$ and the difference between the angle $\alpha$ and $\gamma$ are less or equal to 90° and more than 0°. In another embodiment, the angle differences may be less or equal to 60° and more than 0°. Since the height variation of different human foreheads is within a range, the differences may be further less or equal to 30° and more than 5°. It can be understood that the difference between the angles $\beta$ and $\alpha$ and the difference between the angles $\alpha$ and $\gamma$ may be the same or different. Those skilled in the art may set the angle differences properly according to the practical needs.

The distance between the bottom of the connector matching piece set on each connector and the vertical plane that through the center of the base body is adjustable. The adjustment device can adjusts the position of the forehead fixing device relative to the user's head by adjusting the distance.

Figure 4A:
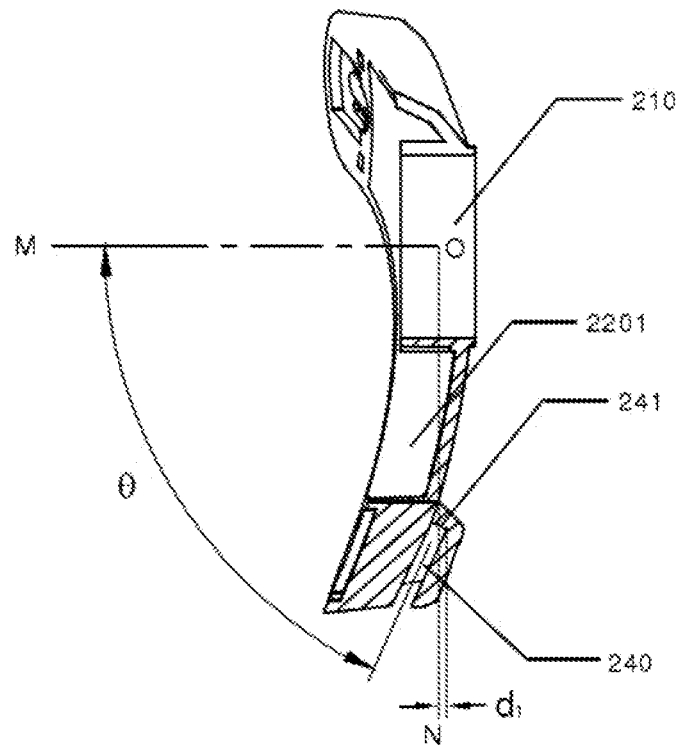
FIG. 4A illustrates the sectional view taken along the A-A line in FIG. 2 in another embodiment of the present invention.
Figure 4B:
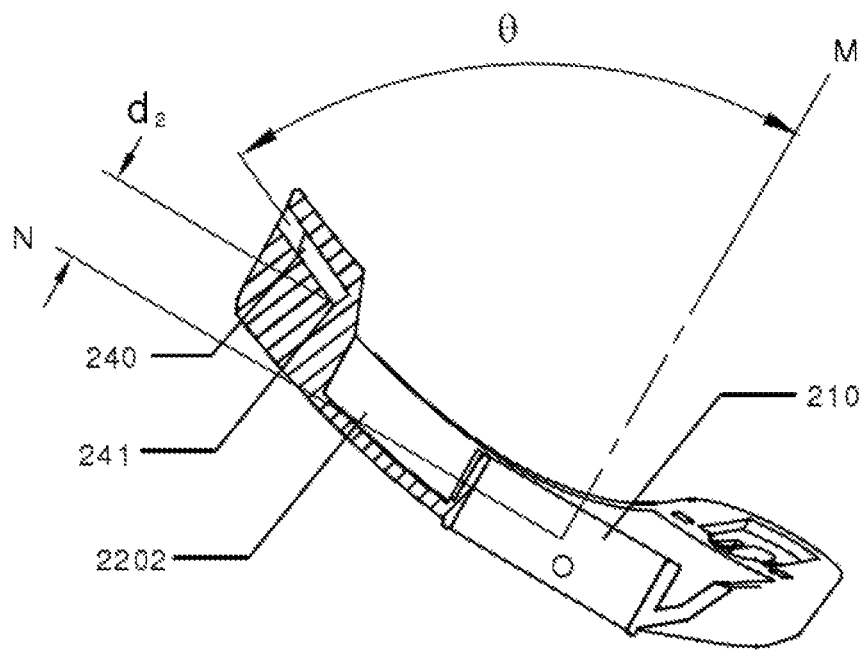
FIG. 4B illustrates the sectional view taken along the B-B line in FIG. 2 in another embodiment of the present invention.
Figure 4C:
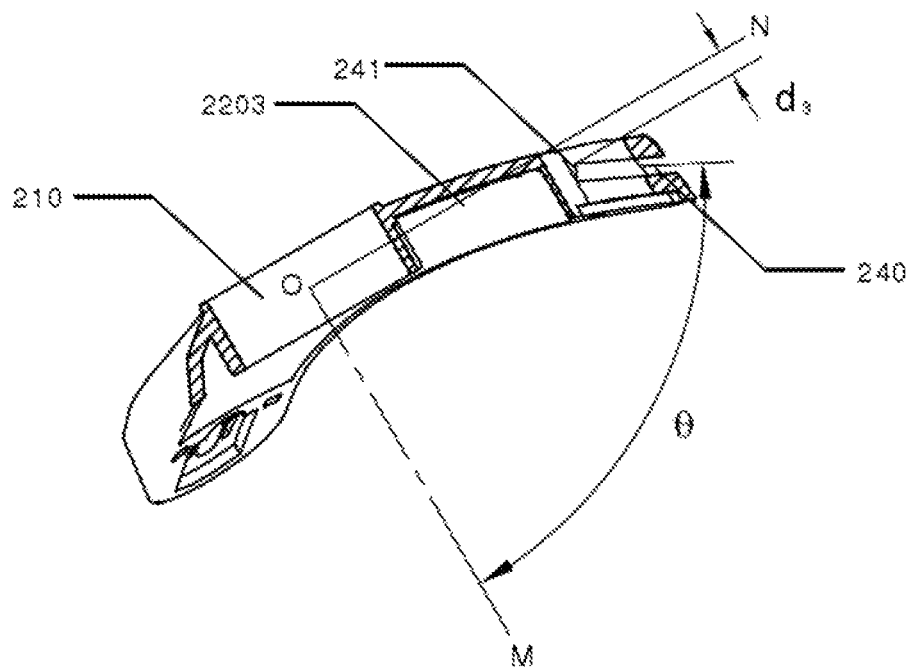
FIG. 4C illustrates the sectional view taken along the C-C line in FIG. 2 in another embodiment of the present invention.

In another embodiment of the present invention, as described in FIG. 4A-4C, the distances between the bottom 241 of each connector matching piece 240 set on each connector (e.g. 2201, 2202 and/or 2203, etc.) and the vertical plane O-N that through the center O of the base body 210 are different. The vertical plane O-N is perpendicular to the horizontal ray O-M and through the center of the base body 210. It should be noticed that, when the bottom 241 of the connector matching piece 240 is located on the inner side of the vertical plane O-N (as shown in FIGS. 4B and 4C), the distance is defined as a negative value, and as the bottom 241 approaches to the vertical plane O-N, the absolute value of the distance decreases. The inner side of the vertical plane O-N represents the side close to the user while the mask is worn. When the bottom 241 of the connector matching piece 240 is located on the outer side of the vertical plane O-N (as shown in FIG. 4A), the distance will be defined as a positive value, and also as the bottom 241 approaches to the vertical plane O-N, the absolute value of the distance decreases. The outer side of the vertical plane O-N represents the side far away from the user while the mask is worn. Therefore, even the absolute values of the distances between bottoms 241 of two connector matching pieces 240 on the two sides of the vertical plane O-N respectively and the vertical plane O-N are the same, the distance values are the opposite numbers, and the distances should be considered to be different in the present invention.

Setting different distances between the bottoms 241 of the connector matching pieces 240 and the vertical plane O-N makes the distance of the forehead fixing device and the user' forehead adjustable, so that the respiratory mask of the present invention can fit different users. Those skilled in the art can understand that, the number of the connectors is not limited to 3 as shown in FIG. 3A-3C, it may be 2, 4 and even more.

Taken following preferable embodiment (where there are three connectors set on the base body) as an example, the structure of an adjustment device will be described with reference to FIG. 4A-4C. In this embodiment, the adjustment device adjusts the location of the forehead fixing relative to the user's head by setting distances between the bottoms 241 of the connector matching pieces 240 set on the connectors respectively and the vertical plane O-N. As shown in FIG. 4A, the distance between the bottom 241 of the connector matching piece 240 of the first connector 2201 and the vertical plane O-N is represented as the first distance d1. Accordingly, as shown in FIG. 4B, the distance between the bottom 241 of the connector matching piece 240 of the second connector 2202 and the vertical plane O-N is represented as the second distance d2. As shown in FIG. 4C, the distance between the bottom 241 of the connector matching piece 240 of the third connector 2203 and the vertical plane O-N is represented as the third distance d3. In an embodiment, the values of the first distance d1, second distance d2 and third distance d3 are different with each other. It should be noticed that the angles between the connector matching pieces 240 set on the first connector 2201, the second connector 2202 and the third connector 2203 and the horizontal ray O-M are the same, as indicated as θ.

Since the settings of the first distance d1, second distance d2 and third distance d3 are related to the structure of the forehead fixing device; those skilled in the art can set the first distance d1, second distance d2 and third distance d3 to proper values according to the structure of the forehead fixing device. The settings of the first distance d1, second distance d2 and third distance d3 will be described in detail according to the structure of the forehead fixing device hereinafter.

Considering that the height difference of users' foreheads is within a certain range, the difference between the first distance d1 and second distance d3 and the difference between the second distance d3 and the third distance d2 are restricted; so that those skilled in the art can properly set the first distance d1, second distance d2 and third distance d3 to make the respiratory mask fit most of users according to the distance differences provided by the present invention and the structure of the forehead fixing device. In an embodiment, the difference between the first distance d1 and second distance d3 and the difference between the second distance d3 and the third distance d2 are less or equal to 50 mm and more than 0 mm. In another embodiment, the difference between the first distance d1 and second distance d3 and the difference between the second distance d3 and the third distance d2 are less or equal to 35 mm and more than 0 mm. Since the height variation of different human foreheads is within a range, the difference between the first distance d1 and second distance d3 and the difference between the second distance d3 and the third distance d2 may be further less or equal to 25 mm and more than 5 mm. It can be understood that the difference between the first distance d1 and second distance d3 and the difference between the second distance d3 and the third distance d2 may be the same or different. Those skilled in the art may set the distance differences properly according to the practical needs.

In another embodiment of the present invention, the angles between the connector matching pieces 240 set on some connectors and the horizontal ray O-M that through the center O of the base body 210 are different. Also, the distances between the bottoms 241 of the connector matching pieces 240 set the other connectors and the vertical plane O-N that through the center O of the base body 210 are also different. By setting different angles and distances, the forehead fixing device can properly keep in touch with the different users' forehead, which makes the respiratory mask fit different users.

A forehead fixing device in an embodiment of the present invention will be described in detail with reference to FIG. 5A to 5B.

Figure 5A:
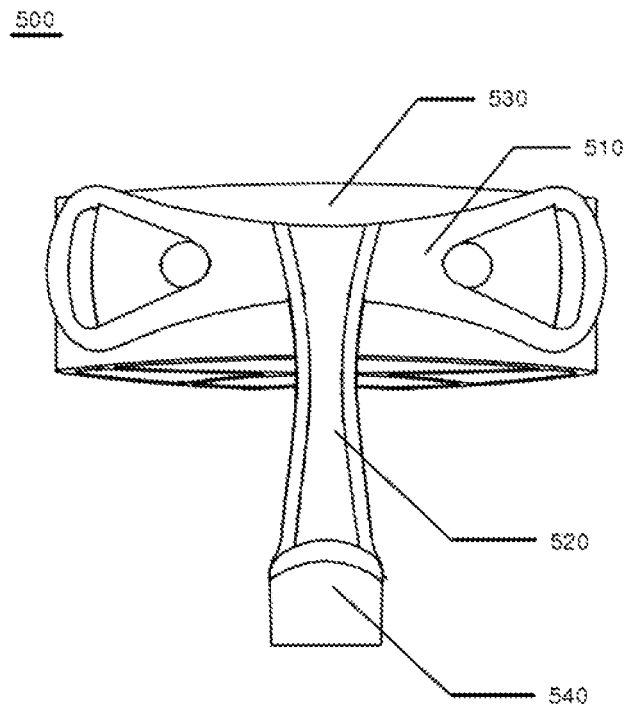
FIG. 5A illustrates the main view of a forehead fixing device in an embodiment of the present invention.
Figure 5B:
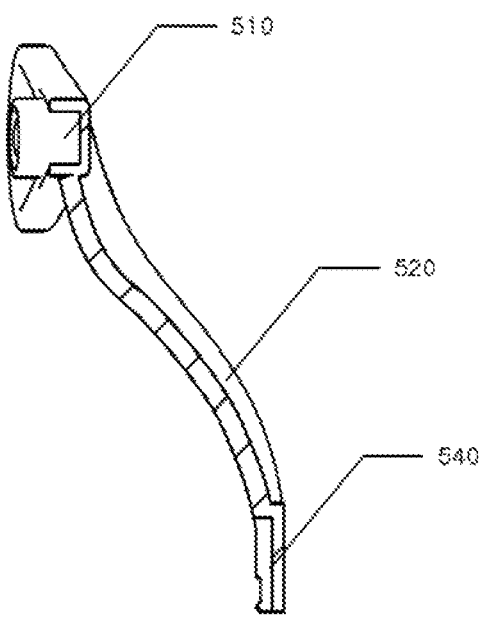
FIG. 5B illustrates the sectional view of a forehead fixing device in an embodiment of the present invention.

FIG. 5A illustrates the main view of a forehead fixing device in an embodiment of the present invention. FIG. 5B illustrates the sectional view of a forehead fixing device in an embodiment of the present invention. As shown in FIGS. 5A and 5B, a forehead fixing device 500 includes a forehead padding part 510 and a fixing part 520. The fixing part 520 is set between the forehead padding part 510 and the adjustment device (shown as 122 in FIG. 1A). Specifically, a first connecting end of the fixing part 520 connects with the forehead padding part 510, and a second connecting end of the fixing part 520 connects with connectors of the adjustment device. The fixing part 520 is preferably ergonomically streamlined, which makes the mask good looking and does not affect the user's other activities while being worn.

When the fixing part 520 is in an ergonomically streamlined shape, if the location of the forehead fixing device relative to the user's forehead is adjusted by setting the angles between the connector matching pieces and the horizontal ray O-M different, the value of the first angle α may be set as 30°≤α<70°, the value of the second angle β may be set as 70°≤β≤85°, and the value of the third angle γ may be set as 85°<γ≤120°; if the location of the forehead fixing device relative to the user's forehead is adjusted by setting the distances between the bottoms of the connector matching pieces and the vertical plane O-N different, the value of the first distance d1 may be set as 10 mm<d1≤30 mm, the value of the second distance d2 may be set as −10 mm≤d2≤10 mm, the value of the third distance d3 may be set as −30 mm≤d3<−10 mm.

Furthermore, to improve the wearing experiences, the forehead padding part 510 may include a forehead pad 530 (not shown in FIG. 5B) that in touch with the user's forehead. It can be understood that, the structure and shape of the forehead padding part 510 and the fixing part 520 (shown in FIGS. 5A and 5B) are only provided as examples, which cannot limit the protection scope of the present invention. Those skilled in the art can reform the forehead fixing device 500 by changing the structures of the forehead padding part 510 and the fixing part 520. All the devices that can fix the respiratory mask on the forehead and be connected with the adjustment device are within the protection scope of the present invention.

Then back to FIG. 1A-1C, since an adaption connector is required to be chosen by the user to be connected with the forehead fixing device 121 and to be adjusted to a proper place (e.g. the adaption connector may be adjusted to the top of the base body when the user wears the respiratory mask at stand pose), the connection between the adjustment assembly 120 and the mask assembly 110 may be flexible so that the location of the adaption connector relative to the user's forehead can be adjusted conveniently, which makes the forehead fixing device in touch with the user's forehead. The flexible connection may be a rotatable connection, a detachable connection or other connections which can make the adaption connector adjusted to the proper place by rotating or moving.

In addition, when there is a through hole 1221 set on the center of the base body of the adjustment device 122 and connected with one end of the air tube 130, a connecting hole (not shown) is set on the mask assembly 110 to connect with the through hole 1221 of the adjustment assembly 120 and the chamber 111 accommodating the nose or snout. It is preferable that the adjustment device 122 rotatably connect with the mask assembly 110 via the connection hole. By setting the through hole 1221 on the center of the base body, setting the connecting hole on the corresponding position of the mask assembly 110 and making the connection between the adjustment assembly 122 and the mask assembly 110 rotatable via the connecting hole, the adaption connector can be conveniently adjusted to the proper place without the interference of the air tube. Furthermore, the structure of the respiratory mask can be simplified, the manufacture cost can be reduced, and the appearance can be more aesthetic consequently.

According to the technical scheme of the present invention, by setting multiple connectors which can be connected to the forehead fixing device and allow an adaption connector to be chosen from the multiple connectors and be connected with the forehead fixing device according to a user's forehead, the respiratory mask can fit different users' foreheads to avoid the air leakage caused by the mask motion during user's sleeping. Furthermore, the structure and manufacture process of the adjustment assembly in the present invention are simplified, less parts or pieces are included, and the costs greatly reduce.

The above description of the embodiments has been used to illustrate the principle of the present invention. It can be understood that, the above embodiments are only provided as examples, which cannot be used to limit the protection scope of the present invention. Those skilled in the art can understand that, the present invention is not limited by the above embodiments; many modifications can be provided under the spirit of the present invention. All of the modifications are within the protection scope of the present invention. The protection scope of the present invention is determined by the claims and the equal protection scope defined by the claims.

The invention claimed is:

1. An adjustment assembly of a respiratory mask, comprising:
    a forehead fixing device, adapted to fix the respiratory mask on a user's forehead; and
        an adjustment device, adapted to adjust a position of the forehead fixing device relative to the user's forehead, comprising a base body, multiple connectors set on the base body and multiple connector matching pieces respectively set on the multiple connectors, each of the multiple connectors is connectable to the forehead fixing device, and the connectors are located on an outer circle of the base body with a same interval in a circumferential direction of the base body, a through hole passing through the center of the base body to connect with one end of an airway tube; and
    wherein when the respiratory mask is worn, only one connector selected from the multiple connectors is connected to the forehead fixing device, wherein each of the multiple connector matching pieces forms an angle with a longitudinal axis of the through hole and each of the angles between each of the multiple matching pieces and the longitudinal axis of the through hole are different from each other.

2. The adjustment assembly of claim 1, wherein, the connection between each of the connectors and the forehead fixing device is detachable.

3. The adjustment assembly of claim 2, further comprising a forehead fixing matching piece set on the forehead fixing device.

4. The adjustment assembly of claim 3, wherein, each of the connector matching pieces and the forehead fixing matching piece respectively are a plug and a groove used for plugging, or a nut and a bolt used for screwing, or a hole and a protruding piece used for snapping.

5. The adjustment assembly of claim 3, wherein, a bandage connector is set on each connector, adapted to be connected with a bandage device.

6. The adjustment assembly of claim 3, wherein, angles between the connector matching pieces and the longitudinal axis are adjustable;
    wherein, the longitudinal axis extends horizontally from a center of the base body, to the user.

7. The adjustment assembly of claim 6, wherein, the adjustment device comprises three connectors and three connector matching pieces respectively set on the three connectors, the angles between the connector matching pieces and the longitudinal axis are represented as a first angle, a second angle, and a third angle respectively;
    wherein, the differences between the first angle and the second angle and between the first angle and the third angle are adjusted to be less than or equal to 90° and more than 0°, or less than or equal to 60° and more than 0°, or less than or equal to 30° and more than 5°.

8. The adjustment assembly of claim 3, wherein, distances between bottoms of the connector matching pieces and a vertical plane that through a center of the base body are adjustable.

9. The adjustment assembly of claim 8, wherein, the adjustment device comprises three connectors and three connector matching pieces respectively set on the three connectors, the distances between the bottoms of the connector matching pieces and the vertical plane are represented as a first distance, a second distance, a third distance respectively;
    the differences between the first distance and the second distance and between the first distance and the third distance are adjusted to be less than or equal to 50 mm and more than 0 mm, or less than or equal to 35 mm and more than 0 mm, or less than or equal to 25 mm and more than 5 mm.

10. The adjustment assembly of claim 1, wherein, the lumber of the connectors is three.

11. The adjustment assembly of claim 1, wherein, the forehead fixing device comprises a forehead padding part and a fixing part; one connecting end of the fixing part connects with the forehead padding part, and another connecting end connects with the one connector.

12. The adjustment assembly of claim 11, wherein, the fixing part is ergonomically streamlined which is curved to fit to the user's face.

13. The adjustment assembly of claim 11, wherein, the forehead padding part comprises a forehead pad, adapted to contact a user's forehead.

14. The adjustment assembly of claim 1, wherein, the through hole is connected via a connecting hole of a mask assembly with a chamber of the mask assembly configured to accommodate a user's nose or snout.

15. The adjustment assembly of claim 14, wherein, the adjustment device rotatably connects with the mask assembly via the connection hole.

16. The adjustment assembly of claim 1, wherein, the base body and connectors are integrated.

17. The respiratory mask of claim 1, wherein, the adjustment device connects rotatable with a mask assembly of the respiratory mask.

* * * * *